(12) United States Patent
Faccioli et al.

(10) Patent No.: US 10,299,932 B2
(45) Date of Patent: *May 28, 2019

(54) ELBOW PROSTHESIS

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 48 days.

This patent is subject to a terminal disclaimer.

(21) Appl. No.: 15/519,913

(22) PCT Filed: Sep. 30, 2015

(86) PCT No.: PCT/IB2015/057494
§ 371 (c)(1),
(2) Date: Apr. 18, 2017

(87) PCT Pub. No.: WO2016/063156
PCT Pub. Date: Apr. 28, 2016

(65) Prior Publication Data
US 2017/0246002 A1 Aug. 31, 2017

(30) Foreign Application Priority Data
Oct. 21, 2014 (IT) .............................. VR2014A0257

(51) Int. Cl.
*A61F 2/38* (2006.01)
*A61F 2/30* (2006.01)

(52) U.S. Cl.
CPC .......... *A61F 2/3804* (2013.01); *A61F 2/3094* (2013.01); *A61F 2002/30472* (2013.01);
(Continued)

(58) Field of Classification Search
CPC ................. A61F 2/3804; A61F 2/4605; A61F 2002/3809; A61F 2002/3813;
(Continued)

(56) References Cited

U.S. PATENT DOCUMENTS 2,696,817 A   12/1954  Prevo
3,816,854 A    6/1974  Schlein
(Continued)

FOREIGN PATENT DOCUMENTS

FR   2 829 688 A1 *  3/2003  ............... A61F 2/38
SU     1532025 A1 * 12/1989  ............... A61F 2/38

*Primary Examiner* — David H Willse
(74) *Attorney, Agent, or Firm* — Tutunjian & Bitetto, P.C.

(57) ABSTRACT

The present invention concerns an elbow prosthesis, including: at least one ulnar section, including a stem portion extending along a substantially longitudinal axis (x-x) between a proximal end and a distal end; at least one humeral section, including a stem portion extending along a substantially longitudinal axis (y-y) between a proximal end and a distal end, the distal end of the humeral section delimiting an engagement seat with the proximal end of the ulnar section; articulation pin between the distal end of the humeral section and the proximal end of the ulnar section, available along an axis (z-z) perpendicular with respect to the substantially longitudinal axis (y-y) of the humeral section. The proximal end of the ulnar section is engageable in the housing seat.

28 Claims, 9 Drawing Sheets

(52) U.S. Cl.
CPC .............. *A61F 2002/30624* (2013.01); *A61F 2002/3813* (2013.01)

(58) Field of Classification Search
CPC ...... A61F 2002/3822; A61F 2002/3827; A61F 2002/3831
USPC ........................................... 623/20.11–20.13
See application file for complete search history.

(56) References Cited

U.S. PATENT DOCUMENTS

2006/0100713 A1  5/2006  Ball
2009/0312840 A1  12/2009  Morrey

\* cited by examiner

ELBOW PROSTHESIS

TECHNICAL FIELD OF THE INVENTION

The present invention concerns a prosthesis for the elbow joint.

STATE OF THE PRIOR ART

The elbow joint, although it is often considered to be a single joint, comprises three separate articulations, associated with a single capsule. These are the humeroradial articulation, the humeroulnar articulation, which allows the bending and extending movements of the forearm on the arm, and the proximal radioulnar articulation, which allows the prono-supination of the hand.

The present invention regards a prosthesis that affects the humeroulnar joint.

STATE OF THE PRIOR ART

Currently for the treatment of lesions of the elbow joint there are joint prostheses which are very complex devices, equipped with numerous components that 15 require long times for the assembly and implantation in the limb of a patient.

The U.S. Pat. No. 3,816,854 discloses a prosthesis for total replacement arthroplasty of the elbow joint consisting of a hinge joint having two intramedullary stems adapted for insertion into the medullary canals of the humerus and the ulna respectively. The free end of one of the stems if formed with an integral partial cylinder within which is secured a cylindrical bearing member formed of ultra high density polyethylene; such cylindrical bearing member has an axial bore for receiving a pivot pin carried on the free end of the other stem. A radial slot in the bearing member, of a width slightly less than the diameter of the pivot pin, allows the pin to be snapped into the bore of the bearing member to form the hinge joint.

The US patent application n. 2006/100713 discloses an elbow prosthesis including an ulnar component which, in turn, includes a first portion defining a longitudinal axis and being implantable in a cavity formed in the ulna and a second portion. Such second portion is rotatably connected to the first portion of the ulnar component about an axis normal to the longitudinal axis. The elbow prosthesis also includes a humeral component including a first portion implantable in a cavity formed in the humerus and a second portion, the latter being operably connected to the second portion of the ulnar component.

The US patent application n. 2009/312840 discloses a prosthetic elbow replacement that includes a humeral component having a stem and a yoke connected to the stem. The yolk terminates in spaced apart arms, between which a pivot pin in mounted for rotational movement with respect to the humeral component. The pivot pin has a transverse through-hole. There is also an ulnar component having an ulnar stem with a proximal end dimensioned to fit within a first end opening of the through-hole. The ulnar component has a mounting cap dimensioned to fit within a second end opening of the through-hole. Moreover, a fastener connects the ulnar stem and the mounting cap such that the proximal end of the ulnar stem is positioned within the first end opening of the through-hole and the mounting cap is positioned within the second end opening of the through-hole. The pivot pin rotates to allow for flexion of the prosthetic elbow replacement and for axial rotation of the ulna component in the humeral component.

Therefore, there is a need to arrange a prosthesis for the elbow joint, which has an alternative configuration with respect to conventional prostheses, which is easy to assemble and implant in the limb of a patient and that ensures good joint functionality.

SUMMARY OF THE INVENTION

The technical task of the present invention is to improve the state of the art in the field of prostheses for the elbow joint.

In the scope of such technical task, one object of the present invention is to provide a prosthesis for the elbow joint, which has an alternative configuration with respect to that of conventional prostheses.

Another object of the present invention is to provide a prosthesis for the elbow joint which allows joint functionality to be maintained, ensuring that the patient has a substantially normal lifestyle.

Yet another object of the present invention is to provide a prosthesis for the elbow joint, which is composed of a reduced number of components.

Not latter object of the present invention is to provide a prosthesis for the elbow joint, which is easy to assemble.

Another purpose of the present invention is to provide a prosthesis for the elbow joint that is safe and cost-effective.

In accordance with one aspect of the present invention, a prosthesis for the elbow joint is foreseen according to the present specification.

In accordance with a further aspect a method of assembly is provided according to the present specification.

The present specification refers to preferred and advantageous embodiments of the invention.

BRIEF DESCRIPTION OF THE DRAWINGS

Further characteristics and advantages of the present invention will be clearer from the detailed description of several preferred embodiments of an elbow prosthesis, illustrated as a non-limiting example in the enclosed drawing tables in which.

In the attached drawings, equivalent parts or components are marked by the same reference numbers.

DETAILED DESCRIPTION OF THE INVENTION

Figure 1:
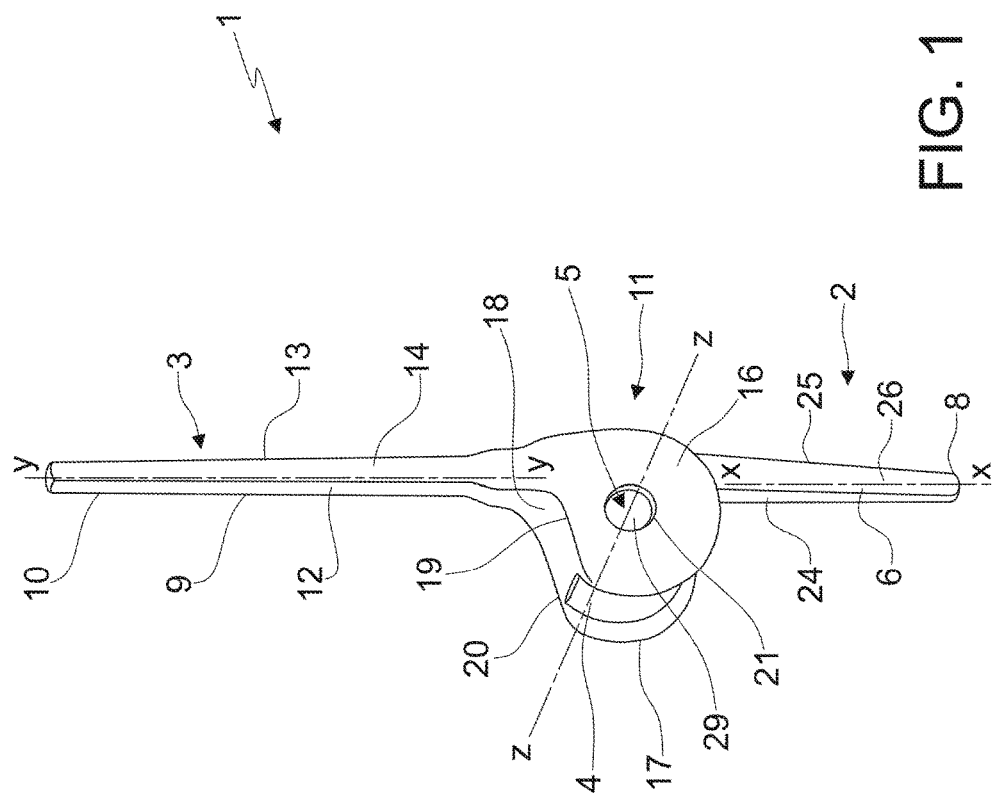
FIG. 1 is a side elevation perspective view of a prosthesis for the elbow joint according to a first embodiment of the present invention.

With reference to the enclosed figures, a prosthesis for the elbow joint according to the present invention, capable of maintaining the joint space and of ensuring the articulation of the elbow of a patient, even when there are serious lesions, is wholly indicated with reference numeral 1.

The prosthesis 1 according to the present invention is made of biologically compatible material with the tissues of the patient.

Such biologically compatible material can be selected among metals, metal alloys, organo-metallic compounds, ceramics or combinations thereof.

The prosthesis 1 can possibly comprise at least one component (which will be described better hereafter) made of plastic or polymeric material, like for example polyethylene.

In a version of the present invention, the biologically compatible material can comprise or be coated with an acrylic resin or a plastic material, a ceramic material, or a highly porous resin, or a combination thereof or a bone cement, for example polymethyl methacrylate (PMMA), or in which the aforementioned plastic or polymeric materials can be selected among thermoplastic polymers, such as acrylic resins, polyethylene, polypropylene, polyester, thermoformable polymers and other similar materials. Such a coating can cover only some or all of the components of the prosthesis or even the portions most subject to rubbing. The coating, when ceramic or acrylic, can comprise, for example, hydroxyapatite, in the case in which it is wished to increase the osteointegration thereof with the bone tissue surrounding the prosthesis.

For the surfaces or the components of the prosthesis 1 most subject to wear, such coating can be made with deposition or application of metal oxides and/or nitrides, like for example titanium nitride, in order to increase the hardness thereof.

The prosthesis for the elbow joint according to the present invention can be made from plastic or ceramic material and comprise a metallic core capable of giving greater stability to the implant, high resistance to loads, etc.

The prosthesis 1 according to a first embodiment of the present invention comprises at least one ulnar section 2, at least one humeral section 3 delimiting an engagement seat 4 and articulation means 5, at such an engagement seat 4, intended to make the engagement and the articulation between the ulnar section 2 and the humeral section 3.

More particularly, the ulnar section 2 has a stem portion 6, which is extended along a substantially longitudinal axis x-x between a proximal end 7 and a distal end 8.

The humeral section 3 has a stem portion 9, which extends along a substantially longitudinal axis y-y between a proximal end 10 and a distal end 11. The distal end 11 of the humeral section 3 delimits, as stated above, an engagement seat 4 with the proximal end 7 of the ulnar section 2.

The articulation means 5 between the distal end 11 of the humeral section 3 and the proximal end 7 of the ulnar section 2, as will be made clearer hereafter, are, in use, arranged in the engagement seat 4, along an axis z-z perpendicular with respect to said substantially longitudinal axis y-y of the humeral section 3. The humeral section 3 of the prosthesis according to the present invention has the stem portion 9 tapered towards its proximal end 10 and has an in use front face 12, an in use rear face 13 and two right and left in use side faces, right and left, respectively indicated in the figures with the numbers 14 and 15.

The distal end 11 of the humeral section 3 is configured to be substantially fork-shaped and comprises two sides 16, 17, a right one and a left one during use, each extended from the stem portion 9 at a respective in use side face, 14 or 15, substantially along the axis y-y.

The distal end 11 of the humeral section 3 also comprises a front wall 18 for connection between the sides 16 and 17 and connected to the stem 9 at the in use front face 12. Such front wall 18 substantially extends in a cantilevered manner from the in use front face 12. The distal end 11 also comprises a rear wall 18' for connection between the sides 16 and 17 and connected to the stem 9 at the in use rear face 13 roughly coplanar therewith.

The sides 16 and 17, the in use front wall 18 and the in use rear wall 18' delimit the engagement seat 4.

Figure 2:
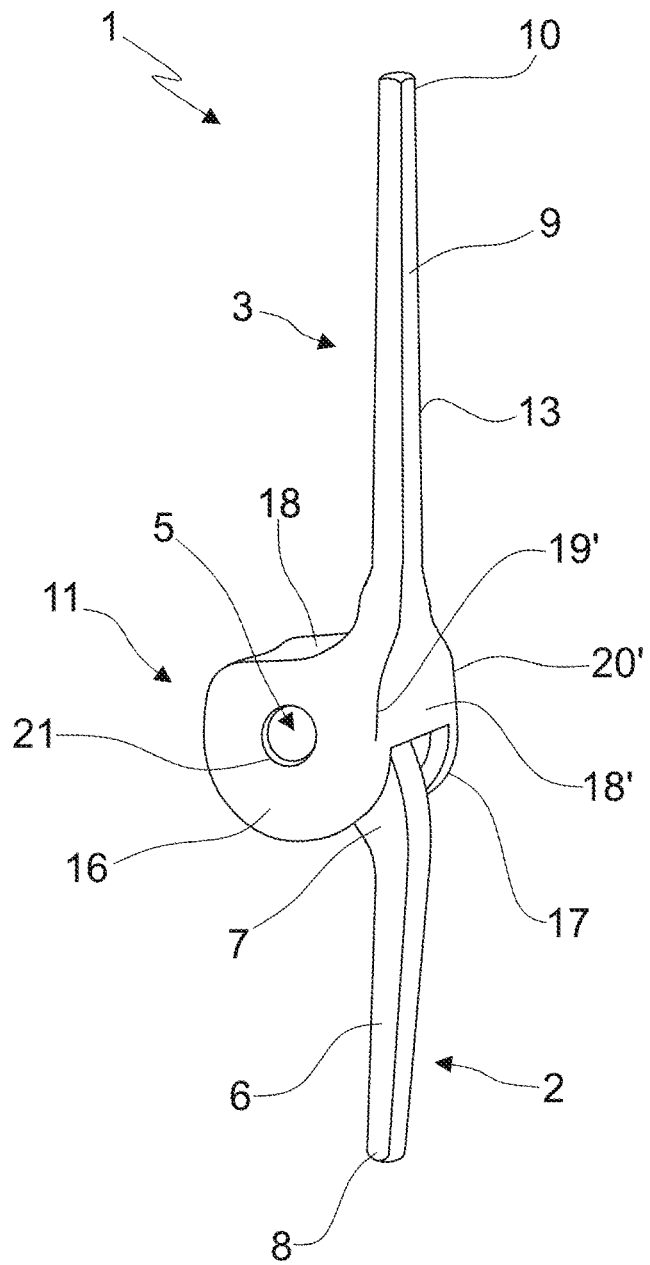
FIG. 2 shows a rear perspective view of the prosthesis of FIG. 1.
Figure 3:
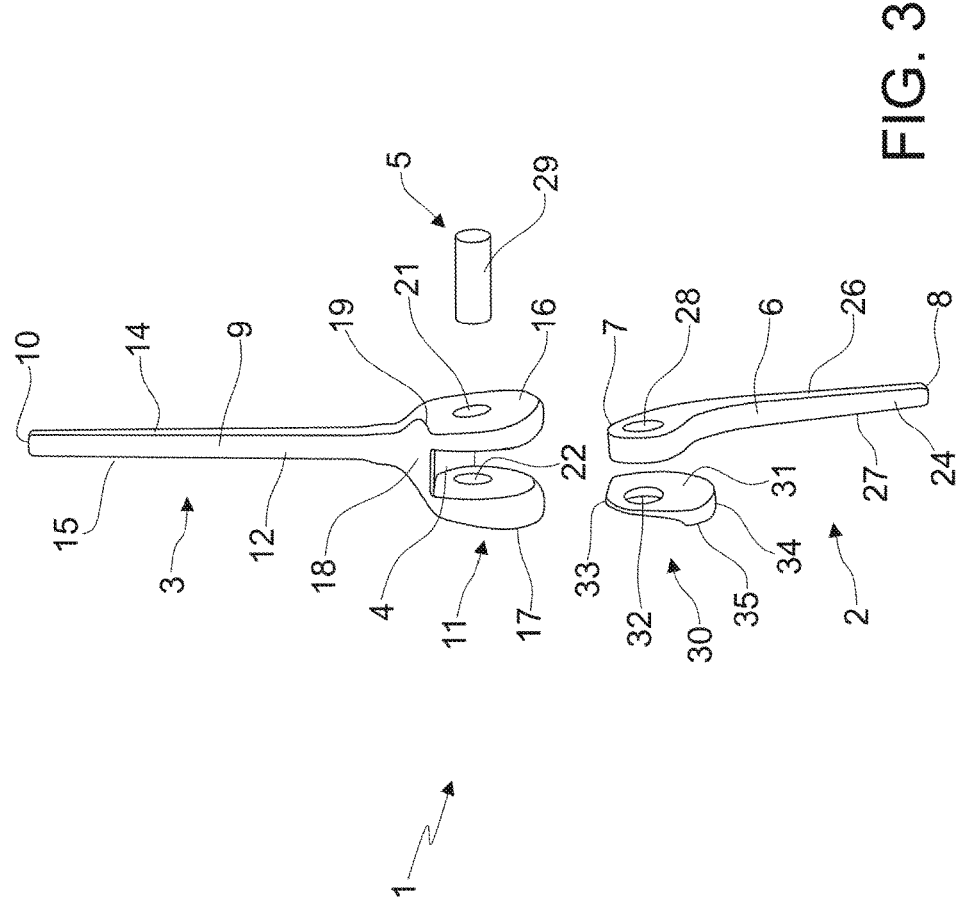
FIG. 3 illustrates an exploded view of the prosthesis of FIG. 1.
Figure 4:
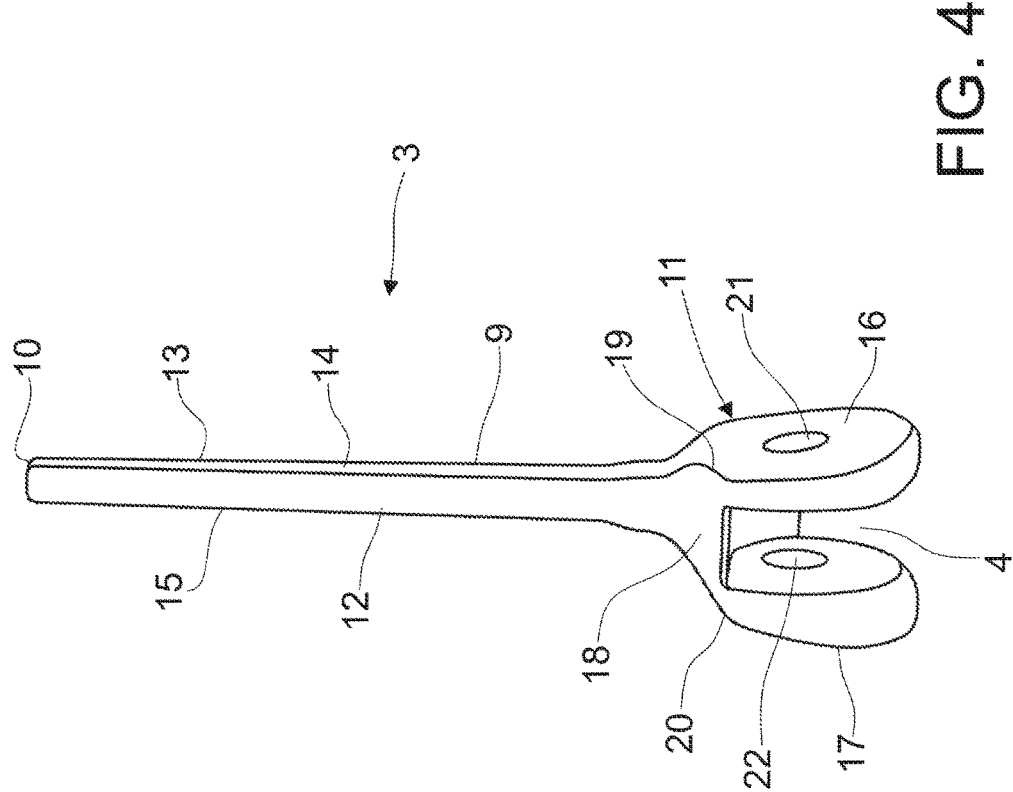
FIG. 4 is a perspective view, in front elevation, of a humeral section of the prosthesis of FIG. 1.
Figure 5:
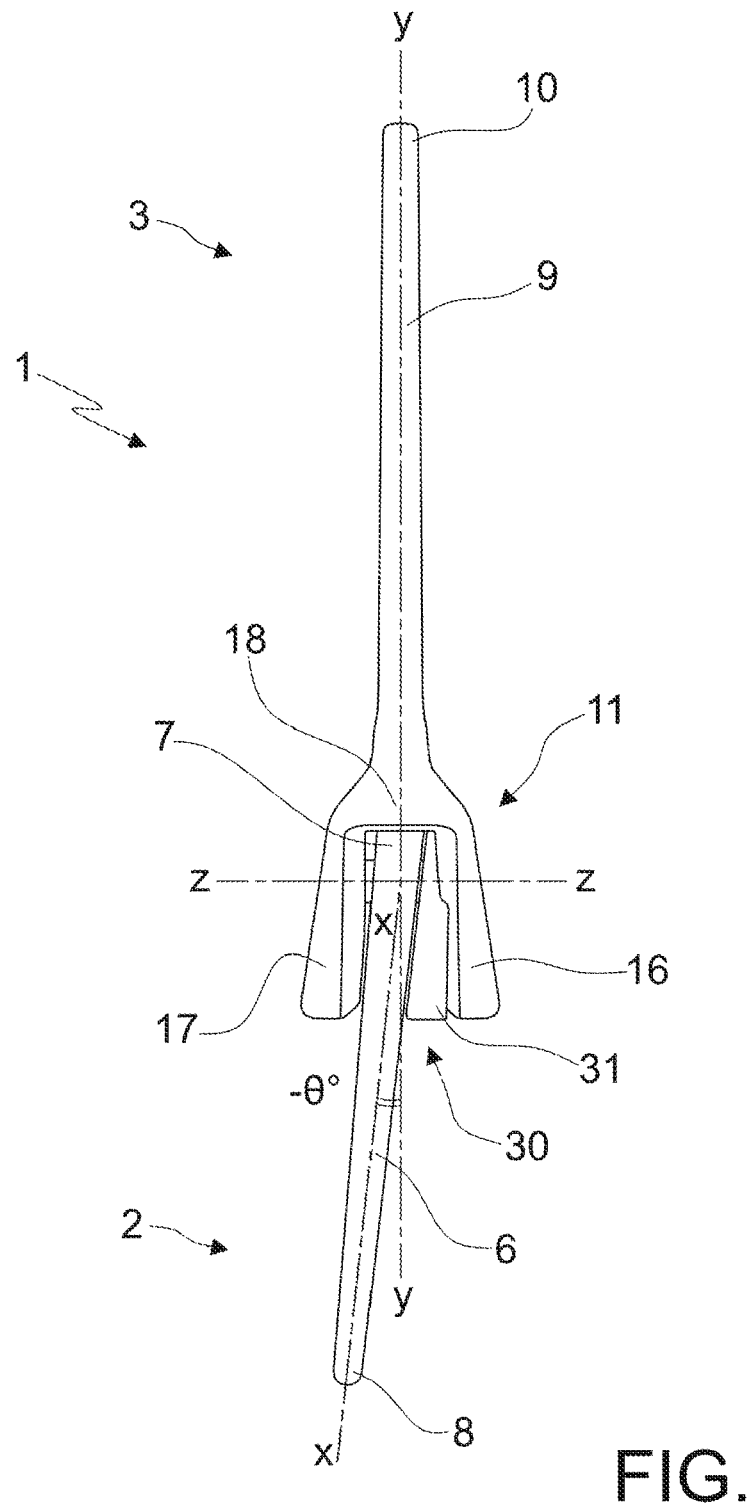
FIG. 5 shows a front view of the prosthesis of FIG. 1, with an ulnar section arranged according to a first working position.
Figure 6:
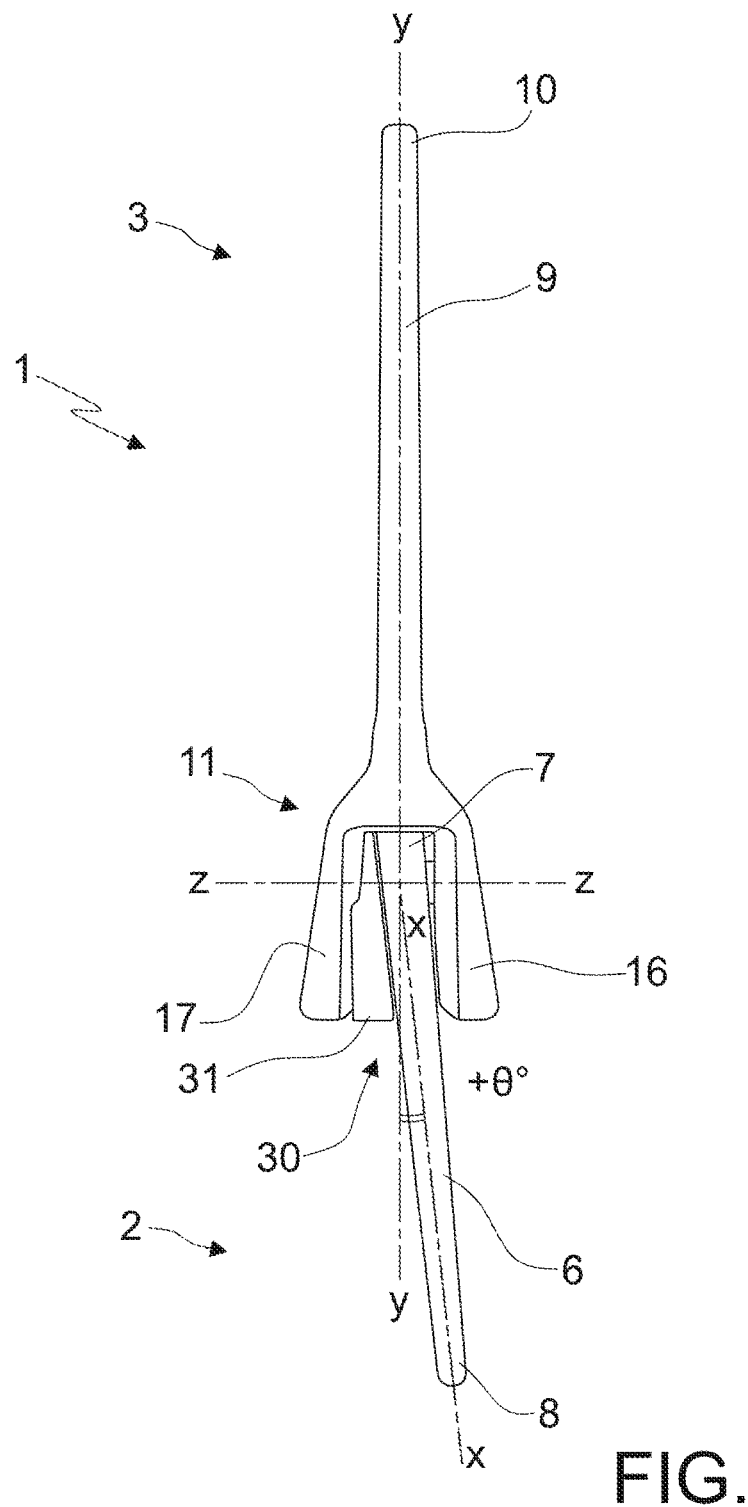
FIG. 6 illustrates a front view of the prosthesis of FIG. 1, with an ulnar section arranged according to a second working position.

As will be observed, each side 16 or 17 of the distal end 11 of the humeral section 3, viewed laterally, has a substantially rounded configuration (FIGS. 1 and 2) with a first substantially rectilinear section 19 or 20 at the connection with the front wall 18 and a second section also substantially rectilinear 19' or 20' at the connection with the in use rear wall 18'. In addition, sides 16 and 17, viewed frontally, have an increasing thickness (FIGS. 3 to 9), moving away from the stem portion 9. Advantageously, the engagement seat 4 also has its own cross section, with respect to the longitudinal axis y-y, increasing moving away from the stem portion 9. With one such configuration, in the engagement seat 4, the sides 16 and 17 are at a minimum distance 23 near the front wall 18 and at a maximum distance at the most extreme points (with respect to the stem 9) of the sides 16 and 17. With one such configuration, it will be easily understood that an optimal distribution is obtained of the forces exerted on the ulnar section 2 and on the humeral section 3 during the use of the prosthesis itself, i.e. during the bending-extending movements of the limb in which such a prosthesis is implanted.

In each side 16, 17 of the distal end 11 at least one through opening 21, 22 is formed, in the example illustrated in the figures a single opening per side. The at least one opening on each side 16 or 17 is aligned with at least one other opening in the other side 17 or 16 of the distal end 11, along a common axis, in the specific case illustrated in the drawings as axis z-z. At such an axis, as will be explained better hereafter, the articulation means 5 are arranged in use. Going back to the ulnar section 2 of the prosthesis 1 according to the first embodiment of the present invention, it possesses its own stem portion 6 tapered towards its distal end 8 and has a front in use face 24, a rear in use face 25 and two right and left side in use faces, respectively indicated in the figures with reference numerals 26 and 27.

Each face 26 and 27, at the proximal end 7 of the ulnar section 2, has a substantially flat and enlarged configuration, with respect to the corresponding distal end 8 of the stem portion. More specifically, at the proximal end 7 each face 26 and 27 is substantially rounded, roughly circular.

As will be noted, see in particular FIGS. 5 to 9, the ulnar section 2 is sized so that the cross-sectional overall dimension of its proximal end 7 is smaller than the minimum cross section dimension (minimum distance 23 in FIG. 7) of the engagement seat 4 of the humeral section 3, so that it is insertable therein with a certain clearance and, more specifically, can be moved with its side face 26 or 27 in contact with one or other side 16 or 17 of the seat itself.

In the ulnar section 2, at the proximal end 7, at least one through opening 28 is formed, which, in use, is intended to receive, as will be discussed more clearly hereafter, the articulation means 5 of the prosthesis 1 according to the present invention.

Figure 7:
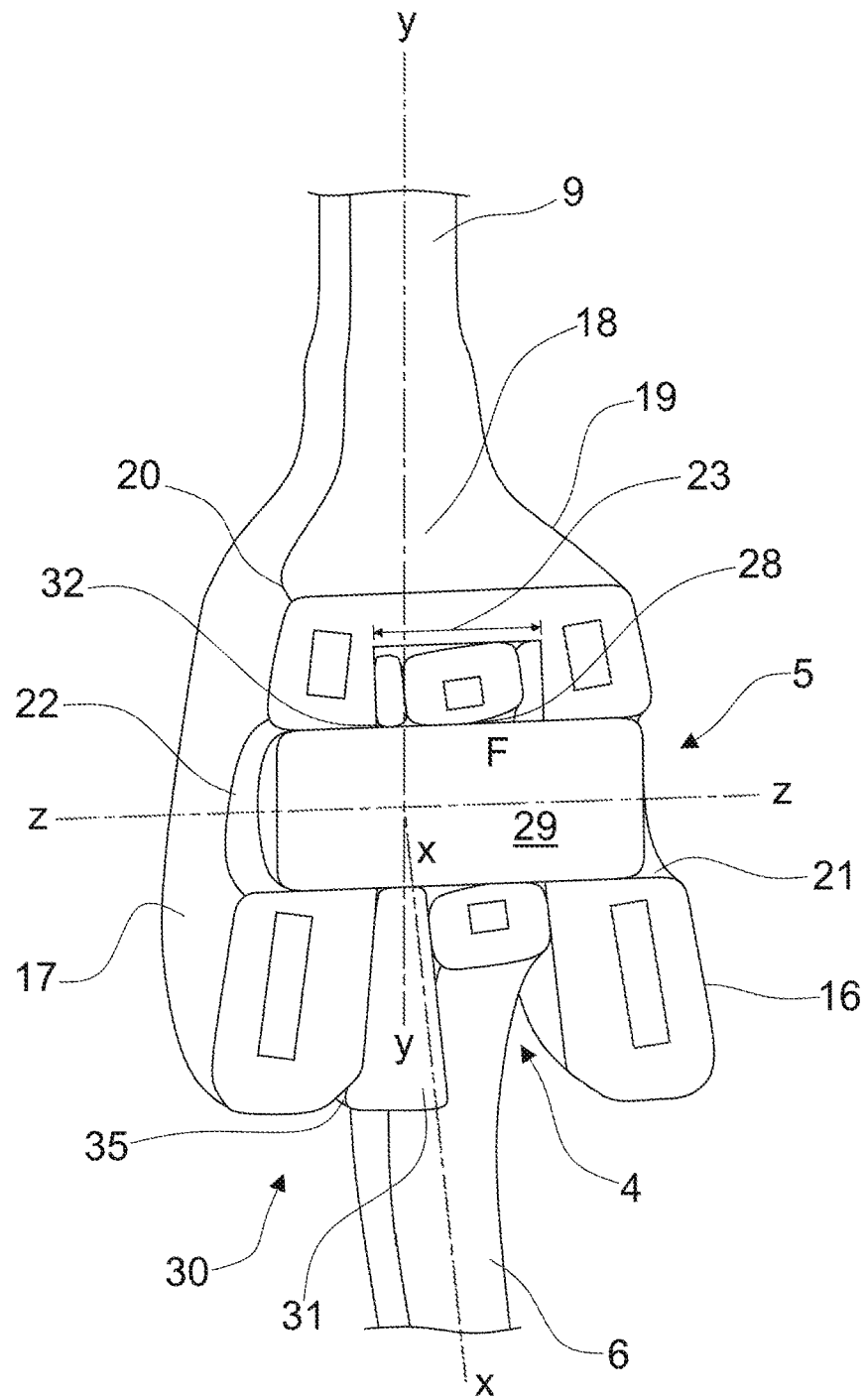
FIG. 7 shows an enlarged scale and cross section view taken along a front plane of the prosthesis according to the first embodiment of the present invention, with the ulnar section arranged according to the second working position.

Such a through opening 28 delimits a gap having a substantially hourglass configuration, i.e. with minimum cross section, indicated in FIG. 7 with the letter F, at a longitudinal symmetry plane (not illustrated in the drawings) of the ulnar section 2 passing through the abovementioned axis x-x. Such gap has increasing cross section moving away from such longitudinal symmetry plane. The articulation means 5 of the prosthesis 1 according to the present invention advantageously comprise at least one pin 29, with cross section corresponding to the minimum gap delimited by the through opening 28 and by the through openings 21 and 22 on the sides 16 and 17 of the distal portion 11 of the humeral section 3.

The pin 29 is therefore engageable with the ulnar section 2, without clearance, only at the minimum cross section of the opening 28. The side wall of the ulnar section 2 delimiting such through opening 28 may or may not touch the pin 29, in accordance with how the ulnar section 2 is, during use, arranged in the engagement seat 4.

Indeed, with one such configuration, the proximal end 7 of the ulnar section 2, inserted in the engagement seat 4, can slightly move along the axis z-z and complete a slight angular travel around a pivot at the minimum cross section of the opening 28, indicated with F.

Therefore, as will be observed, the proximal end 7 of the ulnar section 2 is engageable in the housing seat 4 of the humeral section 2 with its own longitudinal axis x-x not orthogonal to the axis z-z along which the pin 29 is arranged, between at least two opposed working positions, according to whether the prosthesis is intended to be implanted in the right or left upper limb of a patient.

In the first working position (FIG. 5), the proximal end of the ulnar section 2 is situated in the engagement seat 4 adjacent to the side 17 and, therefore, has its own longitudinal axis x-x shifted by −θ° with respect to the axis y-y the humeral section. In this first working position, the prosthesis according to the present invention is suitable for being inserted in the upper right limb of a patient. In the second working position, on the other hand, the proximal end of the ulnar section 2 is in the engagement seat 4 brought up towards the side 16 (FIGS. 6 and 7) and, therefore, has its longitudinal axis x-x shifted by +θ° with respect to the axis y-y of the humeral section. In this second working position, the prosthesis 1 according to the present invention can be used to be inserted in the upper left limb of a patient.

Figure 10:
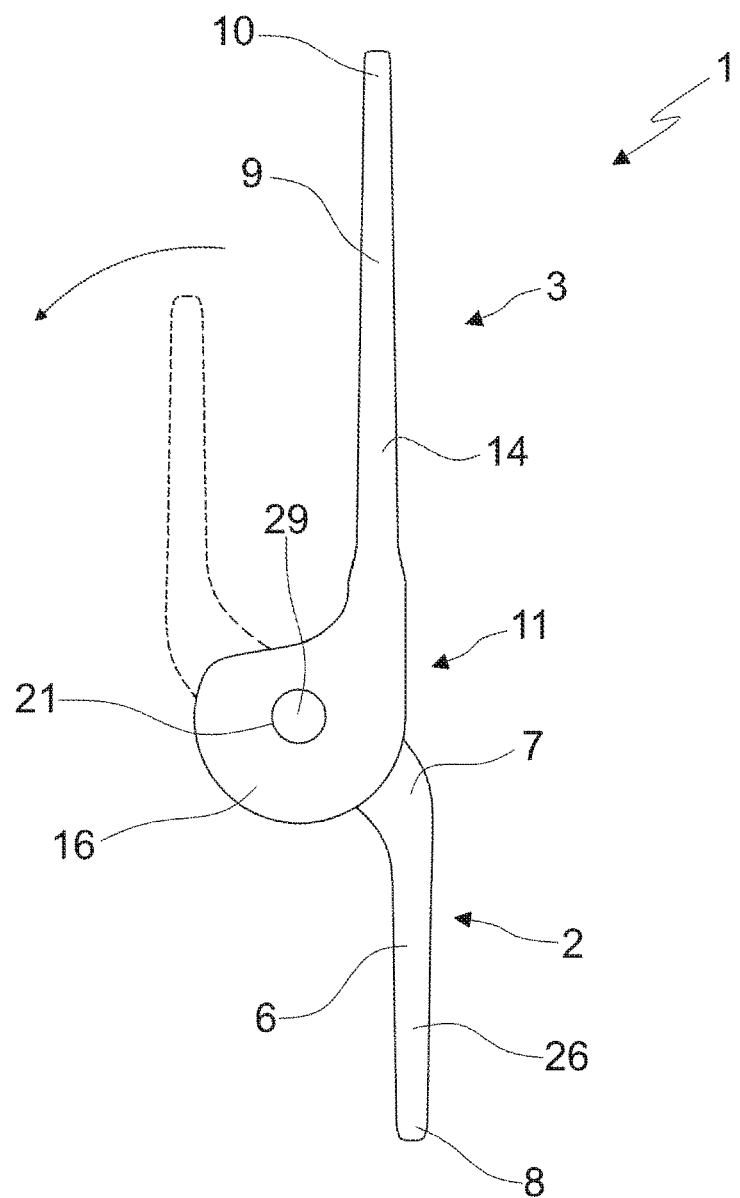
FIG. 10 shows the prosthesis according to the first or the second embodiment in two work positions, one bending and one extending of the prosthesis itself.

Irrespective of the working position taken up by the ulnar section 2, the prosthesis 1 according to the present invention is sized so that the proximal portion 7 of the ulnar section 2, once inserted in the engagement seat 4 of the humeral section 3, and then the pin 29 has been inserted in the through openings 21, 22 and 28 of the sides 16 and 17 and of the ulnar section 2, is rotatable about the pin 29 (as indicated in FIG. 10) between a bending position, in which it substantially faces towards the humeral section 3 and touches the front wall 18, and an extended position, in which it is substantially away from the humeral section 3, aligned with it. As can be seen, the prosthesis 1 according to the present invention allows the ulnar section 2, in the position of maximum extension, to touch the rear in use wall 18' of the humeral section 3. In use, in any case, since such a prosthesis is implanted in patients with reduced humeral-brachial bending, the extension of the forearm on the arm and therefore of the prosthesis is self-limiting and indeed, the ulnar section 2 never touches the rear in use wall 18' of the humeral section 3.

The prosthesis according to the first embodiment of the present invention comprises orienting means 30 of the ulnar section 2 with respect to the humeral section 3, able to be housed in the engagement seat 4.

Such orienting means 30 are foreseen to be arranged, in the engagement seat 4, between the proximal portion 7 of the ulnar section 2 and one or other side 16 or 17 of the seat 4.

Preferably, the orienting means 30 comprise a bushing means, for example made from polyethylene, able to be fitted on the articulation means 5, or any other suitable means capable of keeping the proximal portion 7 of the ulnar section 2 next to one or other side 16 or 17. These include wedge or tilted wall-type means. In the embodiment described and with particular reference to FIGS. 3 and 7 it can be seen how the orienting means 30 are advantageously configured as an annular plate 31 and delimit a through opening 32 of size roughly corresponding to that of the gap delimited by the openings 21 and 22, respectively, on the sides 16 and 17 of the humeral section 3. Such an annular plate 31 can be fitted onto the pin 29 and has a minimum thickness at a proximal section 33 thereof intended, in use, to be housed in the engagement seat 4 facing towards the front in use wall 18 of the humeral section 3. At such a section, the annular plate 31 has a perimeter configuration with straight sections, roughly corresponding to the internal configuration of the seat 4 between the in use front 18 and in use rear 18' walls.

The thickness of the annular plate, on the other hand, is maximum at an opposite or distal section 34, i.e. facing, in use, away from the stem 9 of the humeral section.

The annular plate 31 has its face facing towards one or other side 16 or 17 of the humeral section 3 configured in a manner corresponding to the face of such a side facing towards the engagement seat 4. The annular plate 31, at its opposite or distal section 34, has a flange 35. Such a flange 35 and the configuration of the annular plate 31 at its proximal section 33, as well as the configuration of its side faces contribute to ensuring that it, once housed in the seat 4 and fitted on the pin 29, remains still in position.

With such a configuration of the prosthesis according to the first embodiment of the present invention, it is clear how its assembly is very simple and comprises the operating steps of arranging at least one humeral section 3, at least one ulnar section 2, and at least the aforementioned articulation means 5. Such sections will have size suitable for the articular dimensions of the patient.

It is then foreseen to insert the proximal end 7 of the ulnar section 2 in the engagement seat 4 of the humeral section 3, with the through openings of the respective sections 21, 22 and 28 aligned with each other along a common axis z-z.

Thereafter, if the prosthesis 1 is intended to be implanted in the upper right limb of a patient, the assembly thereof foresees to orient the ulnar section 2, in the engagement seat 4, so that it has its longitudinal axis x-x shifted by an angle −θ°, with respect to the axis y-y of the humeral section 3. Otherwise, if the prosthesis 1 is intended to be implanted in the upper left limb of a patient, the assembly method foresees to orient the ulnar section 2 so that it has its longitudinal axis x-x shifted by an angle +θ°, with respect to the axis y-y.

Once the ulnar section 2 of the prosthesis is brought into the first or second desired work position, the orienting means 30 are inserted in the seat, so as to angularly lock the ulnar section 2 by ±0° with respect to the axis y-y of the humeral section.

In the case in which the orienting means 30 comprise the annular plate 31 as described above, it will be inserted in the engagement seat 4 so that its through opening 32 is aligned with the through openings 21, 22 and 28 along the common axis z-z.

Thereafter, it is foreseen to insert the articulation means 5 (the pin 29) into the aforementioned through openings.

It should be noted that this last insertion step of the articulation means 5 in the openings can also take place before the step of orienting the ulnar section 2, towards one or other of the sides 16 or 17 of the distal portion 11 of the humeral section, in the case in which the orienting means 30 do not necessarily have to be fitted on the pin 29.

Figure 9:
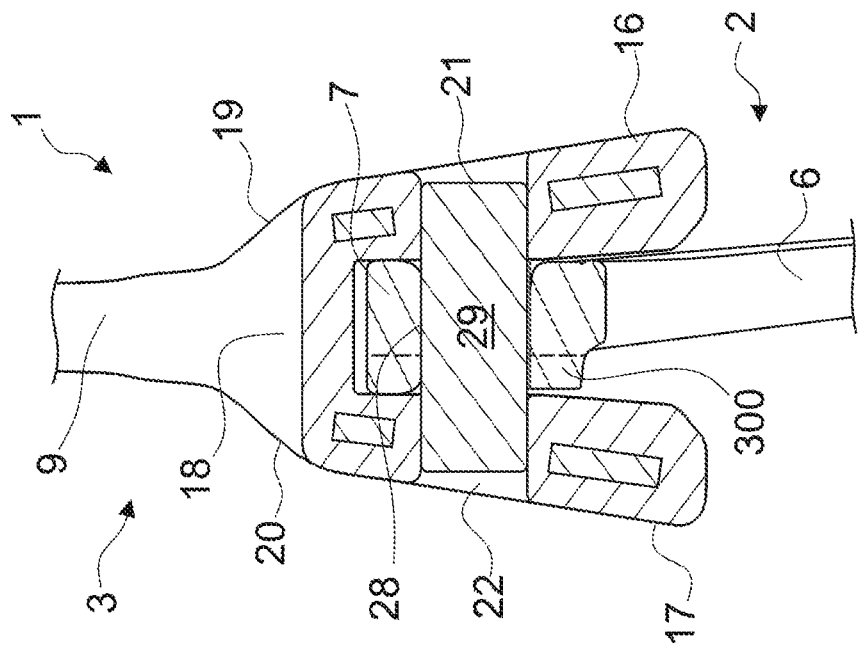
FIGS. 8 and 9 respectively. illustrate a front view of a prosthesis for the elbow joint according to a second embodiment of the present invention and a view thereof in longitudinal section taken along a front plane of the prosthesis itself.
Figure 8:
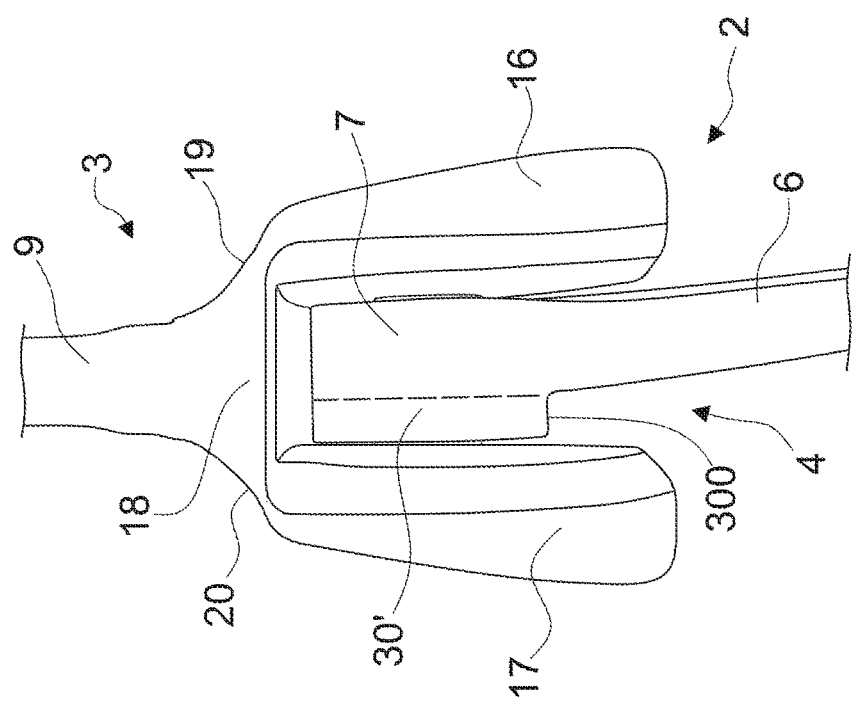

The prosthesis according to the present invention comprises a second embodiment, illustrated in FIGS. 8 and 9, which differs from that of the first embodiment since the ulnar section 2 and the orienting means 30 are made integrally.

In this case, as is clear, the orienting means 300, are also configured as an annular plate 31 and delimit a through opening 32 of size roughly corresponding to that of the openings 21 and 22 on the sides 16 and 17 of the humeral section 3 and of the through opening 28 of the ulnar section 2. Such an annular plate 301, depending on whether the prosthesis must be implanted on the right or left limb of a patient, is foreseen on the face 26 or 27 of the ulnar section itself, so that, depending on the case, the ulnar section is in use, adjacent to the side 16 or 17 of the humeral section 3.

Since, in this case, the orienting means move around the pin 29 together with the ulnar section 2, they have a transversal configuration such as not to prevent the rotation of the ulnar section inside the engagement seat 4. In the specific case illustrated in the figures, the orienting means 300 have a substantially circular crown shaped cross section.

In this second embodiment, as can be noted, the gap delimited by the through opening 28-32 of the ulnar section has a constant cross section.

It has thus been seen how the prosthesis described above clearly solves the aforementioned technical problems, since it has a configuration totally alternative with respect to the conventional prostheses, comprises a small number of components and is also very simple to assemble.

Such a prosthesis, moreover, comprising a stem portion both on the ulnar section 2 and on the humeral section 3, allows it to be in turn inserted in respective bone portions of a patient to be treated, thus ensuring joint mobility.

The prosthesis for an elbow joint 1 described above can undergo numerous modifications and variants within the scope of protection of the following claims.

As can be seen, for example in figure 7, both the ulnar section 2 and the humeral section 3 comprise a stiffening core, preferably made from metallic material, which contributes to making the prosthesis more resistant to stress. Moreover, where possible, for example in the ulnar section 2, in the region comprised between the stem 6 and the proximal end 7, it is possible to form one or more through openings in the stiffening core, which perform the function of reducing the weight thereof, whilst still keeping its mechanical characteristics of resistance to stress unchanged.

Last but not least, depending on the requirements of each case, it is possible to foresee for the stem portion 6 of the ulnar section 2, although extending mainly along the straight axis x-x, to have a medial-distal section misaligned with respect to such an axis, in order to adapt better to the anatomy of the patient under treatment.

The invention claimed is:

1. A prosthesis for the elbow joint, comprising:
   at least one ulnar section, comprising a stem portion extending along a substantially longitudinal axis (x-x) between a proximal end and a distal end, wherein said at least one ulnar section is provided with said stem portion tapered toward said distal end and comprises one front in use face, one rear in use face, and two right and left side in use faces;
   at least one humeral section, comprising a stem portion extending along a substantially longitudinal axis (y-y) between a proximal end and a distal end;
   at least one engagement seat between said distal end of said at least one humeral section and said proximal end of said at least one ulnar section, said at least one engagement seat being delimited by said at least one humeral section; and
   articulation means between said distal end of said at least one humeral section and said proximal end of said at least one ulnar section, positionable along an axis (z-z) orthogonal to said substantially longitudinal axis (y-y) of said at least one humeral section;
   wherein said proximal end of said at least one ulnar section is engageable in said engagement seat with its own longitudinal axis (x-x) nonorthogonal to said axis (z-z) of said articulation means, according to at least two opposed working positions, according to whether said prosthesis is designed to be implanted in the right or in the left upper limb of a patient, and wherein said proximal end of said at least one ulnar portion, viewed laterally, presents a substantially flat and enlarged configuration with respect to the corresponding portion near said distal end, wherein at said proximal end each of said two right and left side in use faces is substantially rounded, roughly circular.

2. The prosthesis according to claim 1, wherein the cross-sectional overall dimension of said proximal end of said ulnar portion is smaller than the cross-section dimension delimited by said engagement seat of said at least one humeral section.

3. The prosthesis according to claim 1, wherein said engagement seat has an increasing cross section, moving away from said stem portion along said longitudinal axis (y-y).

4. The prosthesis according to claim 1, wherein said at least one humeral section is provided with said stem portion tapered toward said proximal end and includes a front, in use, face, a rear in use face, and two left and right in use side faces.

5. The prosthesis according to claim 4, wherein said distal end of said at least one humeral section is configured to be substantially fork-shaped and comprises:
   two sides, in use a right one and a left one, each extending from said stem portion in correspondence with a respective in use side face substantially along said axis (y-y); an in use front wall for connection between said sides connected to said stem at said front, in use, face and substantially extending from it in a cantilevered manner; and an in use rear wall, for connection between said sides connected to said stem at said in use rear face, and substantially extending therefrom along said axis (y-y);

said sides and said in use front wall and said in use rear wall delimiting said engagement seat.

6. The prosthesis according to claim 5, wherein said sides have a substantially rounded shape with a substantially straight section at said connection with said front in use wall and rear in use wall, respectively.

7. The prosthesis according to claim 5, wherein at least one through opening is formed in each side.

8. The prosthesis according to claim 7, wherein said at least one through opening of one of said sides is aligned with said at least one through opening of the other of said sides along an axis, said axis being coincident with said axis (z-z) for said articulation means.

9. The prosthesis according to claim 8, wherein said articulation means comprise at least one pin, the cross-section thereof corresponding to the gap delimited by said aligned through openings in said sides of said distal end of said humeral section.

10. The prosthesis according to claim 9, wherein, between said side in use faces of said proximal end of said at least one ulnar section, at least one through opening is formed defining a gap substantially hourglass-shaped, with a minimum cross section (F) at a longitudinal symmetry plane of said at least one ulnar section including said axis (x-x), and increasing moving away therefrom.

11. The prosthesis according to claim 10, wherein said minimum cross section (F) of said gap delimited by said through opening substantially corresponds to a cross section of a pin, so that said pin is insertable in said through opening, without clearance only at said minimum cross section (F).

12. The prosthesis according to claim 11, wherein said proximal end of said at least one ulnar section, inserted in said engagement seat, can slightly move along said axis (z-z) and complete a slight angular travel at said minimum cross section (F) of said through opening.

13. The prosthesis according to claim 5, wherein said sides have a thickness which increases in a direction away from said stem portion.

14. The prosthesis according to claim 5, wherein said sides are at a minimum distance near said front in use wall.

15. The prosthesis according to claim 5, comprising orienting means of said at least one ulnar section with respect to said at least one humeral section, said orienting means being positionable between said at least one ulnar section and said at least one humeral section in said at least one engagement seat.

16. The prosthesis according to claim 15, wherein said orienting means are placed, in said seat of engagement, between said proximal end of said at least one ulnar section and either one of said sides delimiting said seat.

17. The prosthesis according to claim 15, wherein said orienting means are configured as an annular plate and delimit a through opening of dimensions roughly corresponding to those of through openings of said sides of said humeral section.

18. The prosthesis according to claim 17, wherein said annular plate has a minimum thickness at its own proximal section intended, in use, to be housed in said engagement seat facing said front in use wall of said humeral section.

19. The prosthesis according to claim 18, wherein said annular plate has, at said proximal section, a perimeter configuration with straight sections substantially corresponding to the internal configuration of said seat between said front in use wall and rear in use wall.

20. The prosthesis according to claim 18, wherein said annular plate has a flange in a distal section opposite to said proximal section.

21. The prosthesis according to claim 17, wherein said orienting means are obtained integral with said at least one ulnar section.

22. The method of assembly of a prosthesis according to claim 21, comprising the following steps:

arranging at least one humeral section, at least one ulnar section, at least articulation means between said at least one humeral section and said at least one ulnar section, said at least one ulnar section being integral with said orienting means;

inserting said proximal end of said at least one ulnar section in said engagement seat of said at least one humeral section, with through openings of the respective sections aligned with each other; and inserting said articulation means in said through openings of said at least one ulnar section and at least one humeral section.

23. The prosthesis according to claim 17, wherein said through opening is aligned with a through opening of said at least one ulnar section.

24. The prosthesis according to claim 15, wherein said orienting means have a substantially circular crown shaped cross section.

25. The prosthesis device according to claim 5, wherein in a first working position, said proximal end of said at least one ulnar section is in said engagement seat juxtaposed with said sides and, therefore, has its longitudinal axis (x-x) shifted by −θ° from said axis (y-y) of said humeral section.

26. The prosthesis device according to claim 5, wherein in a second working position, said proximal end of said at least one ulnar section is in said engagement seat juxtaposed with said sides and, therefore, has its longitudinal axis (xx) shifted by +θ° from said axis (y-y) of said humeral section.

27. The prosthesis according to claim 1, wherein between said side in use faces, of said proximal end of said at least one ulnar section, at least one through opening is obtained delimiting a gap having a constant cross section.

28. A method of assembling a prosthesis according to claim 1, comprising the following operating steps:

arranging at least one humeral section, at least one ulnar section, at least articulation means between said at least one humeral section and said at least one ulnar section;

inserting said proximal end of said at least one ulnar section in said engagement seat of said at least one humeral section, with through openings of the respective sections aligned with each other;

if said prosthesis is intended to be implanted in the upper right limb of a patient, arranging said at least one ulnar section so that it has its longitudinal axis (x-x) shifted by an angle of +θ° with respect to the axis (y-y) of said at least one humeral section;

alternatively, if said prosthesis is intended to be implanted in the upper left limb of a patient, arranging said at least one ulnar section so that it has its longitudinal axis (x-x) shifted by an angle of +θ° with respect to the axis (y-y);

inserting orientation means in said engagement seat between said ulnar section and two sides with the respective through opening aligned with through openings; and inserting said articulation means in said through openings of said at least one ulnar section and at least one humeral section.

* * * * *